United States Patent [19]
Aoyama et al.

[11] Patent Number: 5,783,382
[45] Date of Patent: Jul. 21, 1998

[54] METHOD FOR STORING LIQUID DIAGNOSTIC REAGENTS

[75] Inventors: Norihito Aoyama, Gotenba; Minako Sakakibara; Akira Miike, both of Sunto-gun, all of Japan

[73] Assignee: Kyowa Medex Co., Ltd., Tokyo, Japan

[21] Appl. No.: 786,966

[22] Filed: Jan. 24, 1997

[30] Foreign Application Priority Data

Jan. 26, 1996 [JP] Japan ................................. 8-011585

[51] Int. Cl.⁶ .................. C12Q 1/00; C12Q 1/48; C12Q 1/32; C12Q 1/28
[52] U.S. Cl. .................. 435/4; 435/15; 435/26; 435/18; 435/27; 435/28; 435/25; 435/17; 435/14; 435/19; 426/392; 422/50; 422/68.1
[58] Field of Search ................ 435/4, 15, 26, 435/18, 27, 28, 25, 17, 14, 19; 215/26; 422/50, 68.1; 426/392

[56] References Cited

U.S. PATENT DOCUMENTS

| | | | |
|---|---|---|---|
| 4,277,562 | 7/1981 | Modrovich | 435/4 |
| 4,711,741 | 12/1987 | Fujishima et al. | 435/4 |
| 5,381,914 | 1/1995 | Koyama et al. | 435/4 |

FOREIGN PATENT DOCUMENTS

| | | |
|---|---|---|
| 7-223946 | 8/1995 | Japan. |
| 91/02786 | 7/1991 | WIPO. |

OTHER PUBLICATIONS

Database WPI Section CH Week 9520 Derwent Publications Ltd., London. GB; & JP 07 072 158 A (Iatron Lab Inc). 17. Mar. 1995 *Abstract*.

Database WPI, Section CH, Week 9021 Derwent Publications Ltd., London, GB; & JP 02 104 297 A (Amano Pharm KK), 17. Apr. 1990 *Abstract*.

*Primary Examiner*—Louise N. Leary
*Attorney, Agent, or Firm*—Antonelli, Terry, Stout & Kraus, LLP

[57] ABSTRACT

Disclosed is a method for stably storing a liquid diagnostic reagent, comprising air-hermetically keeping the liquid diagnostic reagent in a closed container in the presence of a disoxidant therein. Preferably, at least one of the liquid diagnostic reagent and the disoxidant is covered with a separating container made of a material pervious to oxygen but not to solutions. The liquid diagnostic reagent may comprise an enzyme or an indicator.

12 Claims, No Drawings

METHOD FOR STORING LIQUID DIAGNOSTIC REAGENTS

BACKGROUND OF THE INVENTION

The present invention relates to a method for storing liquid diagnostic reagents as well as a closed container for storing liquid diagnostic reagents.

Liquid diagnostic reagents which are stored and used without being lyophilized have been developed and have greatly been popularized in the field of medical therapy. However, some of enzymes, coenzymes, enzyme activators, substrates, indicators and components derived from living bodies that are a member of diagnostic reagents are often unstable when they are present in a liquid solution, and are therefore difficult to stably store. Accordingly, heretofore, part or all of such substances have been prepared and stored in the form of lyophilizates, which must be dissolved in a liquid solution just before use. To improve the storage stability of liquid diagnostic reagents comprising such unstable substances, known is a method of adding thereto various metal-chelating agents, ultraviolet absorbents, preservatives, reducing agents and stabilizers. However, such method is problematic in that the compounds added to the reagents often have some influences on the aimed detecting reaction. As another method of stabilizing liquid diagnostic reagents without adding thereto any stabilizer, known is a method of stabilizing vitamin C in nourishing and tonifying drinks (see Japanese Published Unexamined Patent Application No. 223946/95).

In order to solve the above-mentioned problems, the present inventors have assiduously studied and, as a result, have found that when a liquid diagnostic reagent is air-hermetically stored in a closed container along with a disoxidant, the storage stability of the liquid diagnostic reagent is surprisingly improved. On the basis of this finding, the present invention has been completed.

SUMMARY OF THE INVENTION

The present invention relates to a method for storing a liquid diagnostic reagent, which comprises keeping the liquid diagnostic reagent in a closed container in the presence of a disoxidant therein.

The present invention also relates to a closed container for storing a liquid diagnostic reagent in which the liquid diagnostic reagent is kept in the presence of a disoxidant therein.

According to the present invention, provided is a simple method of stably storing liquid diagnostic reagents without having any influences on the detecting reaction with the reagents.

DETAILED DESCRIPTION OF THE INVENTION

The disoxidant to be used in the present invention is not specifically restricted, provided that it can absorb oxygen. For example, usable are antioxidants, reducing substances and metal compounds.

The antioxidants include, for example, phenols, amines, hydroxylamines, aldehydes and hydrazines.

The phenols include, for example, monophenols such as phenol, naphthol, butylhydroxytoluene and butylhydroxyanisole; diphenols such as catechol and hydroquinone; triphenols such as pyrogallol, phloroglucinol, gallic acid and its salts; and polyphenols such as lignin and tannin.

The amines include, for example, aliphatic primary amines such as methylamine and ethylamine; aliphatic secondary amines such as dimethylamine and diethylamine; aliphatic tertiary amines such as trimethylamine and triethylamine; aliphatic unsaturated amines such as allylamine and triallylamine; alicyclic amines such as cyclopropylamine and cyclohexylamine; and aromatic amines such as aniline and benzylamine.

The hydroxyamines include, for example, hydroxylamine and methylhydroxylamine.

The aldehydes include, for example, aliphatic saturated aldehydes such as formaldehyde and acetaldehyde; aliphatic dialdehydes such as glyoxal and succinaldehyde; aliphatic unsaturated aldehydes such as acrolein and crotonaldehyde; aromatic aldehydes such as benzaldehyde and naphthaldehyde; and heterocyclic aldehydes such as furfural.

The hydrazines include, for example, hydrazine, methylhydrazine, dimethylhydrazine, and phenylhydrazine.

The reducing substances include, for example, hydrogen compounds, lower oxides, sulfur compounds, phosphorus compounds, arsenic compounds, and organic compounds with lower degrees of oxidation.

The hydrogen compounds include, for example, hydrogen, hydrogen halides such as hydrogen iodide; as well as hydrogen sulfide, lithium aluminium hydride, and sodium borohydride.

The lower oxides include, for example, carbon monoxide, and sulfur dioxide.

The sulfur compounds include, for example, sodium sulfide, polysodium sulfide, ammonium sulfide, and sodium sulfite.

The phosphorus compounds include, for example, yellow phosphorus, and phosphines.

The arsenic compounds include, for example, arsenic.

The organic compounds with lower degrees of oxidation include, for example, ascorbic acid and its salts, isoascorbic acid and its salts; saccharides such as sorbose and glucose; as well as formic acid, and oxalic acid. As examples of the salts, mentioned are salts with metals such as sodium and potassium.

The metal compounds include, for example, metals with high electric positivity, and salts of metals with lower atomic valence.

The metals with high electric positivity include, for example, alkali metals such as lithium, sodium and potassium; as well as magnesium, calcium, zinc, iron, titanium, chromium, tin, and aluminium.

Salts of metals with lower atomic valence include, for example, iron(II) salts, tin(II) salts, titanium(III) salts, and chromium(II) salts. As examples of such metal salts, mentioned are ferrous chloride, and iron sulfide.

Of these disoxidants, preferred are ascorbic acid and its salts, isoascorbic acid and its salts, and disoxidants containing metal powder such as iron powder. Especially preferred are disoxidants containing iron powder.

As such disoxidants containing metal powder such as iron powder, for example, commercial products, "Ageless" (registered trade name, produced by Mitsubishi Gas Chemical Co.), and "Antimold" (registered trade name, produced by Freund Co.) are easily available.

The liquid diagnostic reagent to which the present invention is applied is not specifically restricted. However, it is preferred that the liquid diagnostic reagent comprises at least one of an enzyme and an indicator and optionally contains a reaction substrate for the enzyme, a coenzyme, an activator, a preservative, a stabilizer, a surfactant, a component derived from living bodies, and a buffer.

The enzyme includes, for example, oxidoreductases, transferases, hydrolases, lyase, isomerases, and ligase.

The oxidoreductases include, for example, those acting with a donor, CH—OH; those acting with a donor, aldehyde or oxo group; those acting with a donor, CH—CH; those acting with a donor, CH—$NH_2$; those acting with a donor, CH—NH; those acting on reduced nicotinamide adenine dinucleotide (hereinafter referred to as NADH) or on reduced nicotinamide adenine dinucleotide phosphate (hereinafter referred to as NADPH); those acting with a donor, nitrogen compounds; those acting with a donor, diphenol or its related compounds; those acting with a receptor, hydrogen peroxide; those taking therein molecular oxygen and acting on a pair of donors; and those acting with a receptor, superoxides.

The oxidoreductases acting with a donor, CH—OH include, for example, alcohol dehydrogenase, glucose-6-phosphate dehydrogenase, glycerol dehydrogenase, glycerol-3-phosphate dehydrogenase, 3α-hydroxysteroid dehydrogenase, 7α-hydroxysteroid dehydrogenase, 12α-hydroxysteroid dehydrogenase, isocitrate dehydrogenase, lactate dehydrogenase, pyranose oxidase, glycerol oxidase, alcohol oxidase, choline oxidase, galactose oxidase, glucose oxidase, cholesterol oxidase, L-α-glycerophosphate oxidase, lactate oxidase, D-lactate dehydrogenase, maleate dehydrogenase, phosphogluconate dehydrogenase, fructose dehydrogenase, D-3-hydroxybutyrate dehydrogenase, and mannitol dehydrogenase.

The oxidoreductases acting with a donor, aldehyde or oxo group include, for example, pyruvate oxidase, glyceroaldehyde-3-phosphate dehydrogenase, xanthine oxidase, pyruvate dehydrogenase, and formaldehyde dehydrogenase.

The oxidoreductases acting with a donor, CH—CH include, for example, acyl-CoA oxidase, and bilirubin oxidase.

The oxidoreductases acting with a donor, CH—$NH_2$ include, for example, glutamate synthase, alanine dehydrogenase, tyramine oxidase, amine oxidase, putrescine oxidase, glutamate dehydrogenase, leucine dehydrogenase, and L-amino acid oxidase.

The oxidoreductases acting with a donor, CH—NH include for example, sarcosine oxidase, and sarcosine dehydrogenase.

The oxidoreductases acting on NADH or NADPH include, for example, glutathione reductase, diaphorase, NADH-flavin mononucleotide (hereinafter referred to as FMN) oxide reductase, and NADPH-FMN oxide reductase.

The oxidoreductases acting with a donor, nitrogen compounds, include, for example, uricase.

The oxidoreductases acting with a donor, diphenol or its related compounds include, for example, ascorbate oxidase.

The oxidoreductases acting with a receptor, hydrogen peroxide include, for example, peroxidase, and glutathione peroxidase.

The oxidoreductases taking therein molecular oxygen and acting on a pair of donors include, for example, luciferase, and p-hydroxybenzoate hydroxylase.

The oxidoreductases acting with a receptor, superoxides include, for example, superoxide dismutase.

The transferases include, for example, acyl transferases, glycosyl transferases, and transferases for phosphorus-containing groups.

The acyl transferases include, for example, γ-glutamyl transferase, phospho-transferase, and transglutaminase.

The glycosyl transferases include, for example, purine nucleotide phosphorylase, sucrose phosphorylase, and maltose phosphorylase.

The transferases for phosphorus-containing groups include, for example, creatine kinase, myokinase, hexokinase, phosphoglucomutase, pyruvate kinase, glycerol kinase, acetate kinase, phosphofructokinase, phosphoglycerate kinase, polynucleotide phosphorylase, and phospholipase A2.

The hydrolases includes, for example, those acting on ester bonds; those acting on glycosyl compounds; those acting on peptide bonds; and those acting on C—N bonds except peptides.

The hydrolases acting on ester bonds include, for example, lysophospholipase, cholesterol esterase, phospholipase C, phospholipase D, sphingomyelinase, alkali phosphatase, and lipoprotein lipase.

The hydrolases acting on glycosyl compounds include, for example, glucoamylase, α-glucosidase, β-glucosidase, β-galactosidase, neuraminidase, and invertase.

The hydrolases acting on peptide bonds include, for example, carboxypeptidase, purine iminopeptidase, and pyroglutamyl peptidase.

The hydrolases acting on C—N bonds except peptides include, for example, urease, creatinine amide hydrolase, creatinine deiminase, creatinase, and creatininase.

The lyase include, for example, those acting on carbon-carbon bonds; and those acting on carbon-oxygen bonds.

The lyase acting on carbon-carbon bonds include, for example, N-acetylneuraminate aldolase, and oxaloacetate decarboxylase.

The lyase acting on carbon-oxygen bonds include, for example, enolase, and aconitase.

The isomerases include, for example, racemases, and intramolecular oxidoreductases.

The racemases include, for example, mutarotase.

The intramolecular oxidoreductases include, for example, glucosephosphate isomerase.

The ligase includes those for forming carbon-sulfur bonds; and those for forming carbon-nitrogen bonds.

The ligase for forming carbon-sulfur bonds include, for example, acyl-CoA synthetase.

The ligase for forming carbon-nitrogen bonds include, for example, urea carboxylase.

The indicator includes, for example, color reagents, coloring enzyme substrates, luminescent reagents, fluorescent reagents, and mercapto compounds.

The color reagents are, for example, those that color through oxidation. Of such color reagents, those that react with 4-aminoantipyrine include, for example, phenol derivatives, aniline derivatives, and toluidine derivatives (see Development in Biochemistry and Novel Diagnostic Reagents, by CMC Co., 1984). Also employable herein are chromogens for measuring peroxidase or hydrogen peroxide, which include, for example, leucoindophenol derivatives such as bis[3-bis(4-chlorophenyl)methyl-4-dimethyl-aminophenyl]amine; leucomethylene blue derivatives such as sodium N-(carboxymethylaminocarbonyl)-4, 4'-bis(dimethylamino)diphenylamine, 10-(carboxymethylaminocarbonyl)-3, 7-bis(dimethylamino)phenothiazine (hereinafter referred to as CCAP), 4,4'-bis (dimethylamino)diphenylamine and 10-N-methylcarbamyl-3,7-bis(dimethylamino)-10H-phenothiazine; and triphenylmethane-type leuco dyes.

The coloring enzyme substrates are compounds capable of coloring after having been decomposed with enzyme. As examples, mentioned are compounds that form yellow nitrophenols after having been decomposed with enzyme. Of such coloring enzyme substrates, those, on which β-D-galactosidase and the like act, include, for example, 2-nitrophenyl-β-D-galactopyranoside; and those, on which amylase and the like act, include, for example, 2-chloro-4-nitrophenyl-α-D-maltotrioside.

The luminescent reagents include, for example, luminol, isoluminol, lucigenin, acridinium esters, luciferin, AMPPD (trade name of Tropics Co.), AMPGD (trade name of Tropics Co.) and their derivatives, which are generally used in the field of clinical diagnostic reagents [see Bioluminescence and Chemiluminescence, edited by K. Imai, pp. 82–89, 1989, published by Hirokawa Publishing Co.; Catalogues of Boehlinger Mannheim Co. (1992, 1993)].

The fluorescent reagents include, for example, coumarin, fluorescein, resorufine, aminoacridone, pyrene, diphenylhexatriene, nitrostilbene and their derivatives [see Catalogues of Wako Pure Chemicals Co. (1989)].

The mercapto compounds are of a group of compounds having SH group and include, for example, cysteine, N-acetylcysteine, dithiothreitol, mercaptoethanol, glutathione, coenzyme A (CoA), acetyl CoA and their derivatives, which are useful especially in the field of clinical diagnostic reagents (see Experimental Methods for Biochemistry 10, "Quantitative Determination of SH Group", written by H. Matsumoto & T. Kuninori, published by the Biochemistry Society Publishing Center, 1978).

The coenzyme includes, for example, oxidized or reduced nicotinamide adenine dinucloetide, oxidized or reduced nicotinamide adenine dinucleotide phosphate, FMN, flavin adenine dinucleotide, thiamine diphosphate, pyridoxal phosphate, lipoic acid, folic acid, adenosine triphosphate, adenosine diphosphate, and adenosine monophosphate.

The enzyme activator includes, for example, metal ions, chloride ion, ammonium ion, phosphato ion, sulfato ion, and carbonato ion.

The substrate is those on which enzymes as mentioned above act.

The component derived from living bodies includes, for example, uric acid, bilirubin, hemoglobin, albumin, globulin, and hormones.

The buffer includes, for example, lactate buffers, citrate buffers, acetate buffers, succinate buffers, phthalate buffers, phosphate buffers, triethanolamine buffers, diethanolamine buffers, borate buffers, glycine buffers, barbiturate buffers, tris(hydroxymethyl)aminomethane-HCl buffers, and imidazole-acetate buffers.

The liquid diagnostic reagent may comprise a plurality of enzymes, indicators, coenzymes, enzyme activators, substrates, components derived from living bodies, or buffers.

The shape of the closed container is not specifically restricted. As the material of the closed container, any one that can limit the permeation of oxygen therethrough can be employed. For example, employable are metals, glass, aluminium, aluminium-coated films, and resins. Preferred are glass and resins.

As the resins, usable are polyethylene, polystyrene, polycarbonate, polypropylene, polyvinyl chloride, 6-nylon, and polyethylene terephthalate. However, preferred are resins having a low coefficient of oxygen permeation. As such resins having a low coefficient of oxygen permeation, mentioned are resins having a coefficient of oxygen permeation of less than $0.1 \times 10^{-11}$ cm$^3$ (STP) cm$^{-1}$s$^{-1}$cmHg$^{-1}$, for example, polyvinyl alcohol, polyacrylonitrile, and polyvinylidene chloride.

Especially preferred are air-tight bags having a low coefficient of oxygen permeation, such as polyvinylidene-coated, stretched and nylon/polyethylene double-layered bags "Hiryu" (registered trade name, produced by Saran Wrap Sales Co.).

Where a liquid diagnostic reagent and a disoxidant are air-hermetically kept in a closed container, the method of sealing up them in the container is not specifically restricted.

As the preferred embodiment of sealing up the liquid diagnostic reagent in the container, for example, at least one of the liquid diagnostic reagent and the disoxidant is covered with a separating container made of a material through which oxygen permeates, but the liquid diagnostic reagent does not, and the two are air-hermetically sealed up in a closed container. Where one of the two is thus covered with the separating container and then kept together in the closed container, the liquid diagnostic reagent is not substantially mixed with the disoxidant under any condition of the closed container with the result that the liquid diagnostic reagent is prevented from being contaminated with the disoxidant.

The shape of the separating container is not specifically restricted. The material of the separating container is not also specifically restricted, provided that the container can retain solutions and that oxygen can permeate therethrough. However, preferred are resins. The resins preferably have a coefficient of oxygen permeation of $0.1 \times 10^{-11}$ cm (STP) cm$^{-1}$s$^{-1}$cmHg$^{-1}$ or more, and include, for example, dimethylpolysiloxane, poly(4-methylpentene-1), natural rubber, ethyl cellulose, poly(2,6-dimethylphenylene oxide), polytetrafluoroethylene, low-density polyethylene, polystyrene, polycarbonate, butyl rubber, cellulose acetate, polypropylene, high-density polyethylene, polyvinyl chloride, 6-nylon, and polyethylene terephthalate.

As specific examples of sealing up the liquid diagnostic reagent and the disoxidant in a closed container, mentioned is a method of covering a disoxidant with the separating container as mentioned hereinabove, then putting the separating container into the closed container as mentioned above along with a liquid diagnostic reagent, and sealing up them in the closed container; a method of covering a liquid diagnostic reagent with the separating container as mentioned above, then putting the separating container into the closed container as mentioned above along with a disoxidant, and sealing up them in the closed container; and a method of separately covering both the liquid diagnostic reagent and the disoxidant with different separating containers as mentioned above followed by sealing up them in the closed container as mentioned above.

The amount of the disoxidant to be used in the present invention may be determined, depending on the ability of the disoxidant to absorb oxygen, and the volume of air, especially oxygen, in the closed container. Specifically, the oxygen-absorbing ability of the disoxidant used shall be one or more volumes, preferably two or more volumes, relative to one volume of substantial oxygen in the closed container. Therefore, it is preferred to minimize the amount of air in both the closed container and the separating container. If desired, air in these containers may be substituted with nitrogen gas or the like.

The effects of the present invention are described hereinunder, with reference to the following Examples.

EXAMPLE 1

A color reagent, CCAP was dissolved at 0.1 mg/ml in 100 mM phosphate buffer (pH 6.6) containing 0.1% Triton X-100, to prepare a liquid indicator. 100 ml of this liquid indicator was put into a 100 ml container made of polyvinyl chloride, and sealed up with a screw cap. This was stored at 30° C. under various conditions mentioned below.

Condition (1) for storage:

The polyvinyl chloride container with the liquid indicator therein was stored as it was.

Condition (2) for storage:

The polyvinyl chloride container with the liquid indicator therein was put into a polyethylene bag (140×200 mm), and sealed up.

Condition (3) for storage:

The polyvinyl chloride container with the liquid indicator therein was put into a polyethylene bag (140×200 mm) along with a disoxidant, Ageless S-200 (registered trade name of Mitsubishi Gas Chemical Co.; this has an oxygen absorption capacity of 200 ml), and sealed up.

Condition (4) for storage:

The polyvinyl chloride container with the liquid indicator therein, and a disoxidant, Ageless S-200 were put into a bag made of polyvinyl chloride-coated, stretched nylon/polyethylene, Hiryu KN-204 (registered trade name of Saran Wrap Sales Co.; 140×200 mm), and sealed up.

Each sample was stored under any of the above-mentioned conditions for 1 or 2 weeks, and its absorbance at 666 nm was measured with a spectrophotometer. The data obtained are shown in Table 1. From these, it is known that the indicator samples as air-hermetically stored in the closed container along with the disoxidant were prevented from being oxidized.

TABLE 1

| Condition for Storage | Absorbance (mABS) | |
| --- | --- | --- |
| | After 1 Week | After 2 Weeks |
| Condition (1) | 896 | 2965 |
| Condition (2) | 902 | 2899 |
| Condition (3) | 235 | 521 |
| Condition (4) | 111 | 205 |

EXAMPLE 2

Glucose-6-phosphate dehydrogenase was dissolved at 2.0 U/ml in 100 mM phosphate buffer (pH 6.6) to prepare an enzyme solution. 100 ml of this enzyme solution was put into a 100 ml container made of polyvinyl chloride, and sealed up with a screw cap after air in the container was substituted with $N_2$. This was stored at 30° C. under various conditions as in Example 1. After having been stored for 1 week or 2 weeks under any of such conditions, the residual enzyme activity of glucose-6-phosphate dehydrogenase was measured. The data obtained are shown in Table 2. From these, it is known that the enzyme samples as air-hermetically stored in the closed container along with the disoxidant were stabilized without being inactivated.

TABLE 2

| Condition for Storage | Enzyme Activity (U/ml) | |
| --- | --- | --- |
| | After 1 Week | After 2 Weeks |
| Condition (1) | 0.7 | 0.3 |
| Condition (2) | 0.8 | 0.3 |

TABLE 2-continued

| Condition for Storage | Enzyme Activity (U/ml) | |
| --- | --- | --- |
| | After 1 Week | After 2 Weeks |
| Condition (3) | 1.1 | 0.9 |
| Condition (4) | 1.5 | 1.2 |

EXAMPLE 3

The liquid indicator as prepared in Example 1 was stored for 2 weeks under the condition (3) as in Example 1. In the indicator were dissolved 10 U/ml of peroxidase and 300 µM/liter of hydrogen peroxide, and the solution was allowed to stand at 37° C. for 5 minutes. Then, the change in the absorbance at 666 nm of the sample was measured, using a spectrophotometer. As a control cell (blank), used was the stored sample to which, however, hydrogen peroxide was not added.

As a result, the change in the absorbance of the stored sample was 352 mABS, which was almost the same as the change in the absorbance of the fresh sample, 361 mABS.

On the other hand, the liquid indicator as prepared in Example 1 was stored for 2 weeks under the condition (1) as in Example 1. This was tested in the same manner as above but in vain, resulting in that the change in its absorbance was −14 mABS.

EXAMPLE 4

The liquid indicator as prepared in Example 1 was stored for 2 weeks under the condition (4) as in Example 1. This was tested in the same manner as in Example 3, resulting in that the change in its absorbance was 360 MABS. This value was almost the same as the change in the absorbance of the fresh sample, 361 mABS.

On the other hand, the liquid indicator as prepared in Example 1 was stored for 2 weeks under the condition (2) as in Example 1. This was tested in the same manner as in Example 1 but in vain, resulting in that the change in its absorbance was −1 mABS.

EXAMPLE 5

Liquid reagents for measuring creatine kinase were prepared, which comprised the following components.

| Reagent 1: | |
| --- | --- |
| Imidazole-acetate buffer (pH 6.6) | 115 mM |
| EDTA | 2.3 mM |
| Magnesium acetate | 11.5 mM |
| N-acetylcysteine | 23 mM |
| Dithiothreitol | 10 mM |
| ADP | 2.3 mM |
| AMP | 5.8 mM |
| $AP_5A$ | 11.5 µM |
| Carboxymethoxylamine.HCl | 10 mM |
| Glucose | 23 mM |
| NADP | 2.3 mM |
| Hexokinase or glucokinase | 3.45 U/ml |
| Glucose-6-phosphate dehydrogenase | 1.725 U/ml |
| Albumin | 0.1 mg/ml |
| Reagent 2: | |
| Creatine phosphate | 345 mM |

These liquid reagents of 100 ml each were stored under the condition (3) as in Example 1. Using the stored reagents, creatine kinase in a standard serum sample was quantitatively determined in an ordinary manner.

The data were compared with the value of 100% as determined with the fresh reagents, resulting in that the value as determined with the reagents stored for 1 week was 99.6%, that with the reagents stored for 2 weeks was 92.6%, that with the reagents stored for 3 weeks was 88.5%, and that with the reagents stored for 4 weeks was 80.2%.

On the other hand, the liquid reagents were stored under the condition (1) as in Example 1 and tested in the same manner as above. The data were such that the value as determined with the reagents stored for 1 week was 99.8%, that with the reagents stored for 2 weeks was 87.3%, that with the reagents stored for 3 weeks was 72.5%, and that with the reagents stored for 4 weeks was 62.0%. Thus, the data as obtained with the stored reagents significantly decreased with the lapse of storing time.

EXAMPLE 6

The liquid reagents as prepared in Example 5 of 100 ml each were stored under the condition (4) as in Example 1. Using the stored reagents, creatine kinase in a standard serum sample was quantitatively determined in an ordinary manner.

The data were compared with the value of 100% as determined with the fresh reagents, resulting in that the value as determined with the reagents stored for 1 week was 100.2%, that with the reagents stored for 2 weeks was 98.8%, that with the reagents stored for 3 weeks was 97.3%, and that with the reagents stored for 4 weeks was 96.2%.

On the other hand, the liquid reagents were stored under the condition (2) as in Example 1 and tested in the same manner as above. The data were such that the value as determined with the reagents stored for 1 week was 100.1%, that with the reagents stored for 2 weeks was 88.8%, that with the reagents stored for 3 weeks was 71.3%, and that with the reagents stored for 4 weeks was 60.5%. Thus, the data as obtained with the stored reagents significantly decreased with the lapse of storing time.

As has been described in detail hereinabove, liquid diagnostic reagents can be stably stored according to the method of the present invention.

While the invention has been described in detail and with reference to specific embodiments thereof, it will be apparent to one skilled in the art that various changes and modifications can be made therein without departing from the spirit and scope thereof.

What is claimed is:

1. A method for storing a liquid diagnostic reagent, which comprises keeping the liquid diagnostic reagent in the presence of a disoxidant inside a closed container.

2. The method as claimed in claim 1, wherein at least one of the liquid diagnostic reagent and the disoxidant is covered with a separating container made of a material through which oxygen permeates, but the liquid diagnostic reagent does not.

3. A closed container for storing a liquid diagnostic reagent comprising a container suitable for air-hermetically keeping a liquid diagnostic reagent in the presence of a disoxidant inside the container.

4. The closed container as claimed in claim 3, wherein at least one of the liquid diagnostic reagent and the disoxidant is covered with a separating container made of a material through which oxygen permeates, but the liquid diagnostic reagent does not.

5. The method according to claim 1, wherein the liquid diagnostic reagent comprises a component selected from the group consisting of enzymes, indicators, coenzymes, enzyme activators, substrates and buffers.

6. The method according to claim 1, wherein the disoxidant is selected from the group consisting of antioxidants and metal compounds.

7. The method according to claim 6, wherein the antioxidant is selected from the group consisting of phenols, amines, hydroxyamines aldehydes and hydrazines.

8. The method according to claim 1, wherein the disoxidant is a reducing substance selected from the group consisting of hydrogen, hydrogen halide, hydrogen sulfide, lithium aluminum hydride, sodium borohydride, carbon monoxide, sulfur dioxide, sodium sulfide, ammonium sulfide, sodium sulfite, yellow phosphorus, phosphines and arsenic.

9. The method according to claim 6, wherein the metal compound is selected from the group consisting of lithium, sodium, potassium, magnesium, zinc, calcium, iron, titanium, chromium, tin and aluminum.

10. A method for storing a liquid diagnostic reagent, which comprises keeping the liquid diagnostic reagent in the presence of a disoxidant inside a closed container, wherein the liquid diagnostic reagent comprises at least one of an enzyme and an indicator.

11. A closed container for storing a liquid diagnostic reagent in which a liquid diagnostic reagent is kept in the presence of a disoxidant inside the container, wherein the liquid diagnostic reagent comprises at least one of an enzyme and an indicator.

12. A closed container for storing a liquid diagnostic reagent comprising a container with a liquid diagnostic reagent and a disoxidant therein.

* * * * *